April 3, 1956 W. G. JACKS Re. 24,137

SANITARY PAD

Original Filed Dec. 18, 1952 2 Sheets-Sheet 1

INVENTOR
WILLIARD GRANT JACKS,

BY Bailey, Stephens & Huettig
ATTORNEYS

April 3, 1956 W. G. JACKS Re. 24,137

SANITARY PAD

Original Filed Dec. 18, 1952 2 Sheets-Sheet 2

INVENTOR
WILLIARD GRANT JACKS,

BY Bailey, Stephens & Huettig
ATTORNEYS

United States Patent Office

Re. 24,137
Reissued Apr. 3, 1956

24,137

SANITARY PAD

Willard Grant Jacks, Lynwood, Calif., assignor to International Cellucotton Products Company, a corporation of Delaware Original No. 2,662,527, dated December 15, 1953, Serial No. 326,699, December 18, 1952. Application for reissue September 20, 1955, Serial No. 535,543

6 Claims. (Cl. 128—290)

Matter enclosed in heavy brackets [ ] appears in the original patent but forms no part of this reissue specification; matter printed in italics indicates the additions made by reissue.

The invention relates to absorbent pads for feminine hygiene.

The primary object of the invention is to provide such a pad which gives improved comfort, cleanliness and sanitation to the wearer.

Another object of the invention is to provide a pad which is so conformed to the feminine anatomy as to fit properly and to avoid pressure on adjacent muscle structures.

A further object of the invention is to provide a pad which will not rub contaminants from the rectum or adjacent parts of the body into the vagina.

Still another object of the invention is to provide a pad with a main body portion which is not distorted and compressed by the legs when worn.

An additional object of the invention is to provide a pad which securely seals against the escape of fluid, thus preventing contamination of clothing or other parts of the body and also allowing time for full absorption of the fluid into the pad.

Still a further object of the invention is to provide a pad which has more absorbent material at points where it is effective than those heretofore available, and which thus serves for substantially longer periods of use.

It is also an object of the invention to provide a pad which is very inconspicuous when worn.

Further objects and advantages of the invention will appear more fully from the following description, especially when taken in conjunction with the accompanying drawings which form a part thereof.

Figure 2:
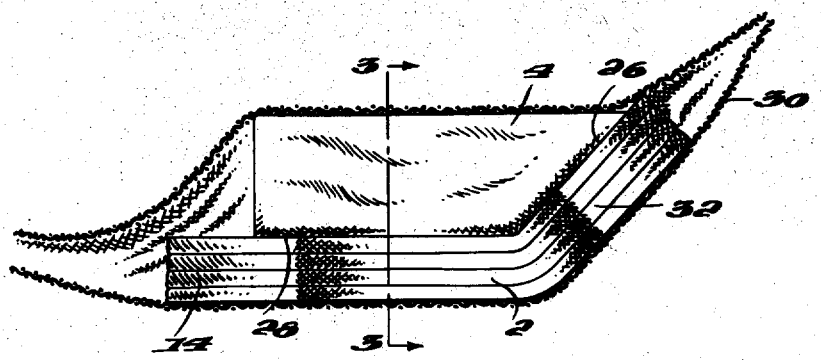
Fig. 2 is a side elevation thereof.

The pad is composed of a main body portion 2 and a second portion 4. Portion 2 is of such length (for example, slightly over six inches) as to extend only from a point forwardly of the rectum 6 (see Figs. 4 and 5), that is a point between the frenulum 8 (*i. e., the rear wall of the vestibule*) and the rectum, (*i. e., the anal area*) to a point opposite the anterior part 10 of the vestibule. The main portion is narrower in the center as at 12 than at its ends 14, 32 (for example, slightly under two inches to slightly over two and a half inches) so that this central portion will remain substantially flat and will not buckle or bend downward between the legs.

Figure 3:
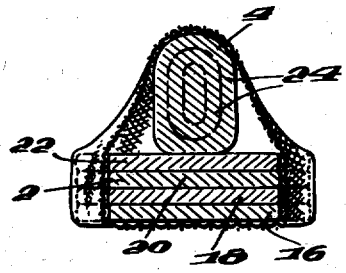
Fig. 3 is a cross-section on the line 3—3 of Fig. 2.

This effect is improved by the fact that the main portion is formed of several parallel layers of absorbent material. For example, as shown in Fig. 3, there may be four layers 16, 18, 20 and 22. Layers 16 and 22 may be formed of several strips of embossed 28-caliper absorbent paper; layer 18 of several similar strips, with an absorbent cotton filler therebetween; and layer 20 of several similar strips with such a filler, whip-cord embossed.

Figure 1:
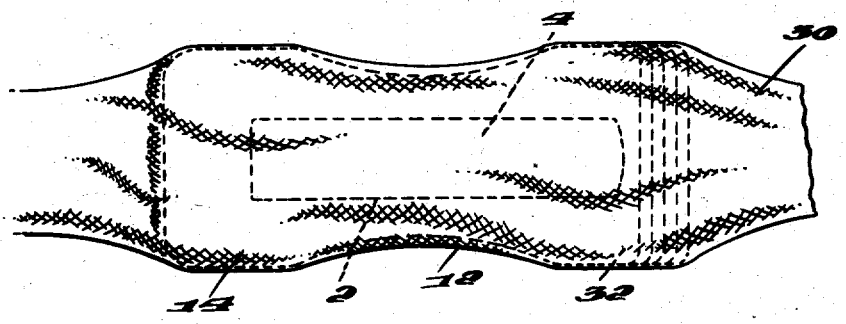
Fig. 1 is a top plan view of a pad embodying my invention.

The second part is formed of one or more layers 24 similar to layer 16 rolled or folded around each other to form a body of somewhat greater height than width. The forward end 26 is slantingly undercut as shown in Fig. 1. This part is substantially centrally positioned on the main body part, but is both shorter and narrower. For example, it may be around four and a half inches long, one inch wide and two inches high.

The two parts may be secured together by crimping the paper layers with each other at the meeting plane 28. The two are enclosed in a tube 30 of gauze which extends beyond the ends of the pad for connection to a belt or supporter to hold the pad in position on the wearer. The front end 32 of the main body portion is folded up against slanting face 26, as shown in Fig. 1.

Figure 5:
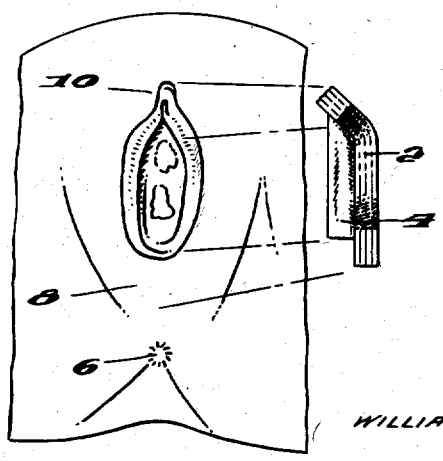
Fig. 5 is an anatomical sketch showing the relation of the pad to the feminine anatomy.

As is shown in Fig. 5, the pad, when properly positioned on the wearer, extends from about the front of the labia minora to the frenulum pudendum. The part [24]4 is of about the length of the vaginal orifice.

Figure 4:
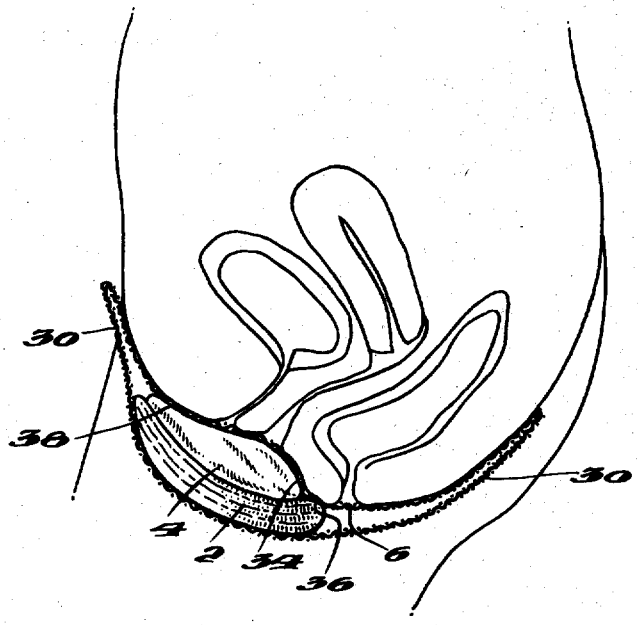
Fig. 4 is an anatomical sketch showing the pad in use.

Fig. 4 shows the effect of such a pad. The rear edge of the small portion will engage the frenulum as at 34, thus providing a damming action which retards leakage of fluid towards the rear. The rear edge of the main body portion will also engage the body at a point 36 forward of the rectum, giving a second damming action and preventing the escape of fluids to the rectal area as well as from such area to the genital organs.

The front edge of the pad engages the anterior portion of the vestibule, as at 38, and thus prevents the escape of fluids toward the front. The smaller pad portion fits at least partially between the labia and absorbs the fluids at their point of emission.

Such a pad creates no pressure on the rectum, and therefore is more comfortable than most pads presently available. It avoids contamination or soiling of other parts of the body and of the clothing by the menstrual fluids, as well as contamination of the genital organs from the rectum. The posterior portion engages the frenulum and extends into the vaginal opening. The anterior portion is flattened and spreads out over the clitoris and adjacent parts so that the pressure is distributed and does not cause discomfort.

The damming action previously described holds the fluids in contact with the pad long enough for them to be properly absorbed therein. Thus escape of the fluids is prevented, and the pad can be worn for a longer time. Also, because of its shortness, it is not discernible when worn.

While I have described herein one embodiment of my invention, I wish it to be understood that I do not intend to limit myself thereby except within the scope of the claims hereto or hereinafter appended.

I claim:

1. An absorbent pad for feminine hygiene, comprising a main body member of absorbent material of a length to extend only from a point between the rectum and the frenulum to the anterior part of the vestibule, and a second member of absorbent material secured on one face of said main member and being narrower and shorter than said first member and being so located on the first member and of such dimensions as to fit between the labia against the vaginal orifice, said first member being wider at its ends than at its center and said second member having a slantingly undercut front end.

2. A pad as claimed in claim 1 in which the main member is formed of layers of absorbent material, all the layers being substantially parallel to one another, and the second member being secured to the first member.

3. An absorbent pad for feminine hygiene, comprising a main body member of absorbent material of a length to extend only from a point between the rectum and the frenulum to the anterior part of the vestibule, and a second member of absorbent material secured on one face of said main member and being narrower and shorter than said first member and being so located on the first member and of such dimensions as to fit between the labia against the vaginal orifice, said second member having a slantingly undercut front end.

*4. An absorbent sanitary napkin for feminine hygiene, comprising an absorbent pad having a main member of absorbent material, a second member of absorbent material on a face of said main member, and a pervious wrapper enclosing said main and second members in said assembled relation and extending beyond the ends of the main member to provide attachment tabs for suspending said pad from a sanitary belt or other supporting garment, said second pad member being narrower and shorter than said main member and being so located on the main member and of such dimensions as to be adapted to fit between the labia and against the wall of the vestibule around the entrance to the vaginal orifice, said second member having a rear end portion of such cross sectional size to, in effect, pack at least a portion of the vestibule so as to cause a portion of said second member to sealingly engage the wall of the vestibule as aforesaid to provide a damming action which retards flow of fluid along said wall and said main member being adapted to engage the body rearwardly of the area of said sealing engagement and forwardly of the rectum to provide a further damming action to further prevent the escape of fluids to the rectal area, said second member having a front end portion of reduced cross sectional size relative to the cross sectional size of said rear portion so that said front end portion may easily be flattened and spread out over the clitoris and adjacent body parts to prevent the production of uncomfortable pressure on said body parts when the napkin is suspended as aforesaid.*

*5. An absorbent pad for feminine hygiene comprising a main member of absorbent material, a second member of absorbent material on a face of said main member, and a pervious wrapper enclosing said main and second members in said assembled relation and extending beyond the ends of said main member to provide attachment tabs for suspending said pad from a sanitary belt or other supporting garment, said second member being so located on said main member and of such dimensions to to be adapted to fit between the labia and against the vaginal orifice, at least the rear end portion of said second member being adapted to be substantially wholly received within the vaginal vestibule in sealing engagement with the regions thereof around the entrance to the vaginal canal, and said rear end portion of said second member being of such cross-sectional size to, in effect, pack the rear portion of the vestibule and thereby maintain said sealing engagement, and said second member having a front end portion of reduced cross-sectional size relative to the cross-sectional size of said rear portion so that said front end portion may easily be flattened out over the clitoris and adjacent body parts to prevent the production of uncomfortable pressure on said body parts when the pad is suspended as aforesaid.*

*6. An absorbent pad for feminine hygiene comprising a main member of absorbent material and a second member of absorbent material on a face of said main member, said second member being so located on said main member and of such dimensions as to be adapted to fit between the labia and against the vaginal orifice, at least the rear end portion of said second member being adapted to be substantially wholly received within the vaginal vestibule in sealing engagement with the regions thereof around the entrance to the vaginal canal, and said rear end portion of said second member being of such cross-sectional size to, in effect, pack the rear portion of the vestibule and thereby maintain said sealing engagement, and said second member having a front end portion of reduced cross-sectional size relative to the cross-sectional size of said rear portion so that said front end portion may easily be flattened out over the clitoris and adjacent body parts to prevent the production of uncomfortable pressure on said body parts when the pad is worn.*

References Cited in the file of this patent or the original patent

UNITED STATES PATENTS

| | | |
|---|---|---|
| 882,301 | Doyle | Mar. 17, 1908 |
| 2,331,355 | Strongson | Oct. 12, 1943 |